United States Patent
Agarwal et al.

(10) Patent No.: US 11,006,848 B2
(45) Date of Patent: May 18, 2021

(54) SYSTEM AND METHOD TO DIAGNOSE AND PREDICT DIFFERENT SYSTEMIC DISORDERS AND MENTAL STATES

(71) Applicants: Puneet Agarwal, New Delhi (IN); Siddharth Panwar, New Delhi (IN)

(72) Inventors: Puneet Agarwal, New Delhi (IN); Siddharth Panwar, New Delhi (IN); Shiv Dutt Joshi, New Delhi (IN); Anubha Gupta, New Delhi (IN)

(*) Notice: Subject to any disclaimer, the term of this patent is extended or adjusted under 35 U.S.C. 154(b) by 579 days.

(21) Appl. No.: 15/544,005

(22) PCT Filed: Jan. 18, 2016

(86) PCT No.: PCT/IB2016/050228
§ 371 (c)(1),
(2) Date: Jul. 16, 2017

(87) PCT Pub. No.: WO2016/113718
PCT Pub. Date: Jul. 21, 2016

(65) Prior Publication Data
US 2017/0367607 A1    Dec. 28, 2017

(30) Foreign Application Priority Data
Jan. 16, 2015  (IN) .......................... 2008/DEL/2014

(51) Int. Cl.
| A61B 5/0476 | (2006.01) |
| G06K 9/00 | (2006.01) |
| A61B 5/16 | (2006.01) |
| A61B 5/00 | (2006.01) |

(52) U.S. Cl.
CPC ............ *A61B 5/0476* (2013.01); *A61B 5/165* (2013.01); *G06K 9/00496* (2013.01); *A61B 5/7239* (2013.01); *A61B 5/7257* (2013.01)

(58) Field of Classification Search
None
See application file for complete search history.

(56) References Cited

U.S. PATENT DOCUMENTS

| 6,697,660 | B1* | 2/2004 | Robinson | A61B 5/04005 324/248 |
| 2003/0031597 | A1* | 2/2003 | Sota | A61B 5/1455 422/82.09 |
| 2004/0133119 | A1* | 7/2004 | Osorio | A61B 5/048 600/544 |
| 2004/0267152 | A1* | 12/2004 | Pineda | A61B 5/048 600/544 |
| 2006/0251303 | A1* | 11/2006 | He | A61B 5/04008 382/128 |
| 2008/0208072 | A1 | 8/2008 | Fadem et al. | |
| 2009/0054740 | A1 | 2/2009 | Gudmundsson et al. | |

(Continued)

*Primary Examiner* — Etsub D Berhanu

(57) ABSTRACT

The present invention relates a novel system and method to diagnose and predict systemic disorders including brain disorders and mental states in early stage and more accurately. More particularly, this invention relates to a novel method of EEG recording and processing through which multiple output data streams are taken together from a system like brain and the structure of their correlation matrix is studied through its eigenvector, eigendirection and eigenspaces and other signal processing techniques including compression sensing, wavelet transform, fast fourier transform etc.

8 Claims, 7 Drawing Sheets

(56) References Cited

U.S. PATENT DOCUMENTS

| | | | |
|---|---|---|---|
| 2009/0076357 A1* | 3/2009 | Purdy | A61B 17/12113 600/347 |
| 2009/0124923 A1* | 5/2009 | Sackellares | A61B 5/048 600/544 |
| 2009/0220429 A1 | 9/2009 | Johnsen et al. | |
| 2010/0069776 A1* | 3/2010 | Greger | A61B 5/685 600/544 |
| 2010/0286747 A1 | 11/2010 | Sabesan et al. | |
| 2013/0274625 A1 | 10/2013 | Sarma et al. | |

* cited by examiner

FIG. 3

|   | 1 | 2 | 3 | 4 | 5 | 6 | 7 | 8 | 9 |   |
|---|---|---|---|---|---|---|---|---|---|---|
| 1 | 1013.035 | 772.4686 | 1010.943 | 1306.416 | 1069.249 | 1126.309 | 994.4431 | 962.749 | 983.8137 | Cz |
| 2 | 772.4686 | 930.7475 | 958.2692 | 1371.434 | 905.3931 | 1029.344 | 750.9833 | 836.0429 | 786.7128 | Fp2 |
| 3 | 1010.943 | 958.2692 | 1322.706 | 1629.754 | 1301.435 | 1363.969 | 1142.621 | 1096.675 | 1115.698 | F4 |
| 4 | 1306.416 | 1371.434 | 1629.754 | 2368.216 | 1694.967 | 1831.514 | 1461.635 | 1495.445 | 1403.401 | F8 |
| 5 | 1069.249 | 905.3931 | 1301.435 | 1694.967 | 1685.329 | 1566.096 | 1451.442 | 1331.021 | 1412.942 | C4 |
| 6 | 1126.309 | 1029.344 | 1363.969 | 1831.514 | 1566.096 | 1734.303 | 1450.451 | 1422.764 | 1381.981 | T4 |
| 7 | 994.4431 | 750.9833 | 1142.621 | 1461.635 | 1451.442 | 1450.451 | 1612.988 | 1361.478 | 1497.77 | P4 |
| 8 | 962.749 | 836.0429 | 1096.675 | 1495.445 | 1331.021 | 1422.764 | 1361.478 | 1559.591 | 1265.041 | T6 |
| 9 | 983.8137 | 786.7128 | 1115.698 | 1403.401 | 1412.942 | 1381.981 | 1497.77 | 1265.041 | 1617.376 | O2 |
|   | Cz | Fp2 | F4 | F8 | C4 | T4 | P4 | T6 | O2 |   |

Response Vector

SYSTEM AND METHOD TO DIAGNOSE AND PREDICT DIFFERENT SYSTEMIC DISORDERS AND MENTAL STATES

FIELD OF THE INVENTION

The present invention relates a novel system and method to diagnose and predict systemic disorders including brain disorders and mental states in early stage and more accurately. More particularly, this invention relates to a novel method of EEG recording and processing through which multiple output data streams are taken together from a system like brain and the structure of their correlation matrix is studied through its eigenvector, eigendirection and eigenspaces and other signal processing techniques including compression sensing, wavelet transform, fast fourier transform etc.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders. EEG measures voltage fluctuations resulting from ionic current flows within the neurons of the brain. In clinical contexts, EEG refers to the recording of the brain's spontaneous electrical activity over a short period of time, usually 20-40 minutes, as recorded from multiple electrodes placed on the scalp. Diagnostic applications generally focus on the spectral content of EEG, that is, the type of neural oscillations that can be observed in EEG signals.

The importance of accurate, timely diagnosis of brain abnormality is crucial in many clinical settings including the emergency room (ER) or intensive care unit (ICU), in Out-Patient Department (OPD). However, most mental and neurological states are evaluated mainly through interviews and subjective exams based on the subjects' temporary performance at that time. There is no objective quantitative test for evaluating baseline brain function. Imaging technologies such as standard magnetic resonance imaging (MRI) show only structure within the brain without providing an indication of dynamic brain function. EEG is the most effective method for evaluating brain function like ECG for the heart, but interpretation requires interpretation of multichannel graphs based on visual analysis by highly trained experts.

Currently the EEG is used to diagnose neurological disease like epilepsy, seizures, encephalopathy, comatosed condition, brain dead state, encephalitis (brain fever). It is very useful tool in comatosed or unconscious patient to know the reason of unconsciousness. But it is not very sensitive and specific for the different diseases most of the time. The sensitivity varies from 30% to 60% in patients of epilepsy. EEG is often normal in patients having recent seizures even on the same day of the test. EEG is not specific or sensitive in patients of stroke, dementia, Parkinson's disease or encephalopathy.

The present invention overcomes the above shortcomings by providing a novel methodology which will be helping in diagnosing the different disorders including neurological and also systemic diseases more accurately and comprehensibly. It will also diagnose certain neurological disorders, which are not diagnosed with current EEG techniques and predict them even before symptoms.

OBJECT OF THE INVENTION

The main object of the present invention is to provide a novel system and method to diagnose and predict different diseases specially brain disorders and mental states in early stage and more accurately.

Yet another object of this invention is to provide a novel system and method to predict the systemic disorders even before symptoms.

Yet another object of this invention is to provide a novel system and method to predict the neurological disorders even before symptoms.

Yet another object of this invention is to provide a novel method of EEG recording and processing.

Yet another object of this invention is to diagnose and predict different brain disorders and study mental states by recording EEG in a novel manner.

Yet another object is to determine the basic principle of neuronal functioning as a system operating on different signals whether linear system or non-linear system.

Yet another object of this invention is to analyze the EEG recording using eigenvalues, eigenvectors, eigendirections and eigenspaces and other signal processing techniques like Fast Fourier transform, compression sensing, wavelet transform etc.

Yet another object of this invention is to use the Spinal EEG and suboccipital lead as additive source of EEG signals and to evaluate spinal EEG in diagnosing the diseases and to know the primary source of EEG signals.

Yet another object of this invention is to create and use 4 dimensional EEG images to predict the different disease in early stage.

Still another object of this invention is to record EEG non invasively from the surface of the brain bypassing the skull bone for diagnosing specific brain disorders by using advanced signal processing techniques and to know skull transfer factor.

Yet another object is to determine the basic principle of neuronal functioning and understand the generation and evaluation of thought process.

SUMMARY OF THE INVENTION

Accordingly, the present invention relates a novel system and method to diagnose and predict systemic disorders including brain disorders and mental states in early stage and more accurately. More particularly, this invention relates to a novel method of EEG recording and processing through which multiple output data streams are taken together from a system like brain and the structure of their correlation matrix is studied through its eigenvector, eigendirection and eigenspaces and other signal processing techniques including fast fourier transform, compression sensing, wavelet transform etc.

In a preferred embodiment of the present invention eigenvectors/eigenvalues, properties of inner product spaces and 4D visualization of EEG signal's statistical, temporal and spectral properties is proposed to diagnose various systemic disorders in any subject. The proposed system analyses the EEG signals and giving values for three parameters each for left and right side of the brain, namely, ρ, θ, and h, which represent the underlying mathematical structure of the signals appearing on the scalp. The three parameters are then plotted with time to give the novel 4 dimensional visualization of the entire EEG activity of the brain.

The values of ρ, and θ, of EEG signals for one hour are also plotted which are unique for the individual and are helpful in predicting/diagnosing different disorders/diseases. The EEG analysis reflects different chemical, molecular and channel abnormalities in different diseases.

In another preferred embodiment of the present invention, a diagnostic kit for EEG based diagnosis of systemic and neurological disorders is proposed. The kit comprises a means for data input, a processing unit, and an output device. Characterized in that, the processing unit provides 4 dimensional visualization of brain activity resulting into projection of possibilities of systemic and neurological disorders.

In another preferred embodiment of the present invention EEG signals were also analyzed from patent of hemicraniectomy and compared from one hemisphere having normal skull bone from other hemisphere having no bone. It reflects skull transfer function, which may be useful in making EEG signal interpretation more accurate.

In another preferred embodiment of the present invention EEG signals from spine (Spinal EEG) and suboccipital area were analyzed using advanced signal processing techniques in normal and different diseases as well as near to brain dead patients. It showed promising and interesting results showing which may be helpful in knowing primary source or master point of EEG signals as wells as predicting different diseases.

BRIEF DESCRIPTION OF DRAWINGS

A complete understanding of the device and system of the present invention may be obtained by reference to the following drawings:

FIG. 3 shows the raw data of the signals represented in FIG. 2 that are used as input for the algorithm.

DETAILED DESCRIPTION OF THE INVENTION

Figure 1:
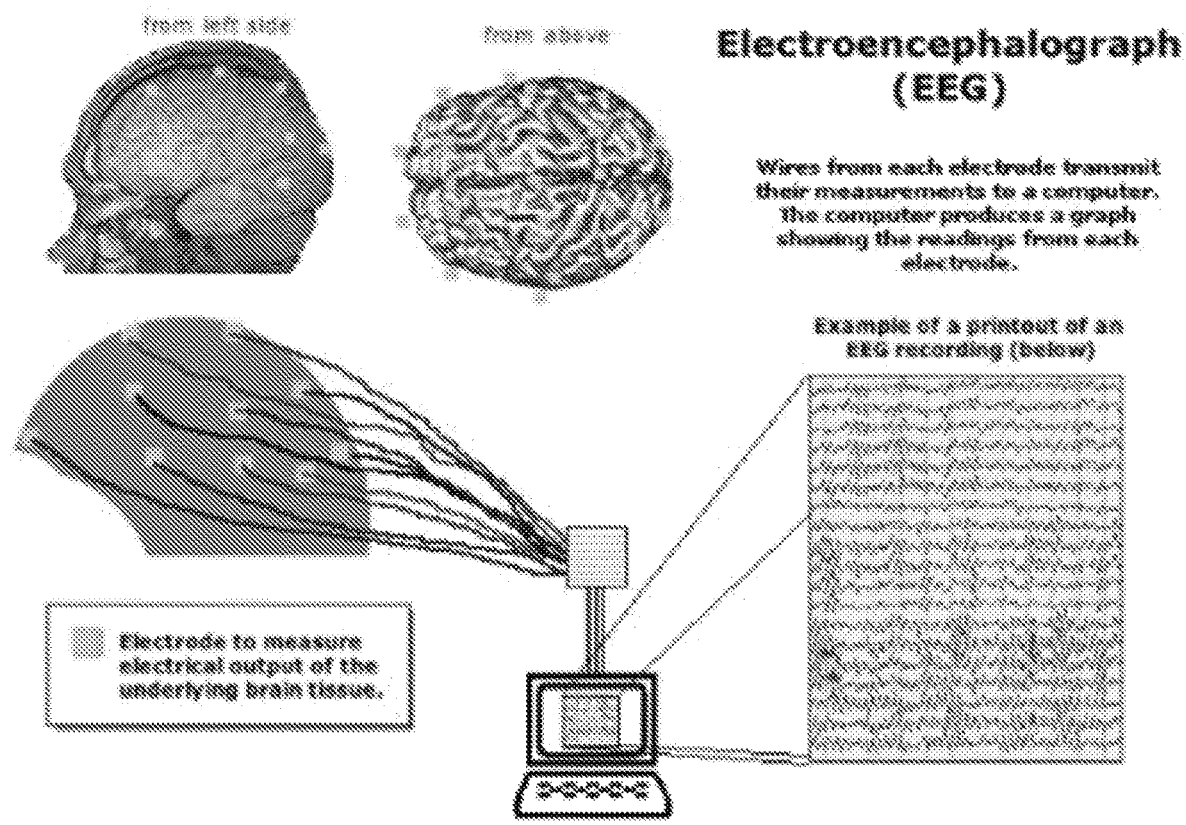
FIG. 1 shows a general overview of procedure of recording EEG signals.

The present invention relates to a novel system and method to diagnose and predict different brain disorders and mental states. More particularly, this invention relates to a novel method of EEG recording and processing through which multiple output data streams are taken together from a system like brain and the structure of their correlation matrix is studied through its eigenvalues, eigenvector, eigendirection and eigenspaces and other signal processing techniques like compression sensing, wavelet transform etc.

The present invention involves creating a correlation matrix from EEG signals obtained in a fixed duration of time from the various locations of the scalp. The dynamics of the eigenvector together with the eigenvectors is studied to characterize brain function. People suffering from brain disorders have a greater rigidity in the dynamic behavior of their eigenvectors and that allows in diagnosing such different behavior more accurately and comprehensibly.

In one aspect, the present invention is a novel EEG product which is composed of unique method of EEG recording and processing. The EEG product involves EEG recording by using spinal EEG and different scalp EEG electrodes. The EEG analysis is done by a unique process in which output data streams are taken together from a system like brain and the structure of their correlation matrix is studied through its eigenvector, eigenvalues, eigendirection and eigenspaces and other signal processing techniques like compression sensing, wavelet transform etc.

These EEG data are analyzed by other signal processing techniques like wavelet transform, compression sensing. Further, analysis of the skull bone transfer factor is done by analyzing EEG data taken from hemicraniectomy patients in which one half of the skull bone has been removed. This method effectively characterizes the transfer function of scalp bone data with high accuracy. EEG is also recorded using different photic signals from two sources and then analyzed to determine the basic principle of neuronal functioning as a system operating on different signals whether linear system or non-linear system.

Yet another aim is to determine the basic principle of neuronal functioning as a system operating on different signals whether linear system or non-linear system.

This method also useful in predicting certain neurological disorders and different systemic disease, which are not diagnosed with the current EEG techniques.

In another aspect, the methodology of recording and processing EEG signals from multiple output data streams, comprising of the following steps:
  i. Performing EEG of patient scalp including suboccipital as well as spinal electrodes. The EEG is done in normal patients, patients of epilepsy, dementia, deep coma, severe head injury, stroke, Parkinson's disease;
  ii. EEG is analysed with different signal processing techniques like eigenvalues, eigenvectors, eigendirections, wavelet transform, fast fourier, compression sensing technologies;
  iii. functional modeling and 4 D functional imaging of brain is done by using said techniques; and
  iv. Skull bone transfer factor is analysed using these data.

This brain model is validated in different neurological disorders for predicting as well as diagnosing the diseases in early stages so that prevention and proper treatment can be done more effectively.

Thus, the proposed system and method is capable of early detection of brain disorders, mental states and different diseases of body. The system and method provides for diagnosis of epilepsy for patients not having classical diagnostic markers in EEG. It further measures the severity of the neurological disease/disorder as well as monitors the progression of a neurological disorder. The system and method helps source localization (focal) of epileptic activity and other brain disorders/abnormalities and seizure prediction to be used in advanced warning systems for epilepsy patients. The system and method uses eigenvectors/eigenvalues, properties of inner product spaces and 4D visualization EEG signal's statistical, temporal and spectral properties to diagnose patients.

In another preferred embodiment of the present invention, a diagnostic kit based on the inventive concept of the present invention is proposed. The kit comprises at least a means for data input, a processing unit to process the data, and at least one output device to present the processed data as the result or diagnosis. The diagnostic kit is capable of early detection of brain disorders, mental states and different diseases of body. The kit provides for diagnosis of epilepsy for patients not having classical diagnostic markers in EEG. It further measures the severity of the neurological disease/disorder as well as monitors the progression of a neurological disorder. The kit helps source localization (focal) of epileptic activity and other brain disorders/abnormalities and seizure prediction to be used in advanced warning systems for epilepsy patients. The kit uses eigenvectors/eigenvalues, properties of inner product spaces and 4D visualization EEG signal's statistical, temporal and spectral properties to diagnose patients.

According to an embodiment of the invention proposed through this specification, the diagnostic kit for early detection of human disorders comprises:
 a. a means for sensing brainwaves of a user;
 b. a means for recording pattern of the brainwaves of the user;
 c. a means for processing the pattern recorded in step b., the means capable of performing an analysis of the brainwave pattern resulting into a four dimensional visualization; and
 d. a means for representing four dimensional visualization of the entire EEG activity of the user's brain obtained in step c.;
characterized in that the analysis of brainwave pattern is done by giving values for three parameters each for left and right side of the brain, namely, $\rho$, $\theta$, and h, and plotting them with time to give the four dimensional visualization of brain activity.

In an alternate embodiment of the present invention, a method of EEG based diagnosis for early detection of human disorders is suggested, the method comprising the steps of:
 a. recording EEG signal data to obtain a brainwave pattern;
 b. optionally grouping the signals obtained in step a. into at least two groups;
 c. breaking the signal data into frames;
 d. creating covariance matrix of each frame obtained in step c.;
 e. computing eigenvectors and eigenvalues;
 f. computing response vector covariance matrix from its eigenvectors and eigenvalues;
 g. reducing the covariance matrix to three dimensional spherical coordinate parameters;
 h. plotting the three dimensional parameters as a function of time to obtain four dimensional visualization of the EEG signals of step a.; and
 i. observing distribution pattern of the parameters for deviation;
wherein any deviation in distribution pattern is indicator of abnormality.

Further, the signal data comprises at least 100 samples of each signal per second, and each group comprises plurality of signals. The frame comprises data consisting of at least 100 samples, of all the signals in each group taken separately. In a preferred mode, covariance matrix is a symmetric matrix constructed with the signals obtained and at least 100 samples for each signal. An eigenvector of a matrix is a vector which when multiplied by that matrix results in a scaled version of the original vector itself and the eigenvectors and eigenvalues are computed by equation $Ax_i = \lambda_i x_i$, where $x_i$ is one of the eigenvectors of A and $\lambda_i$ is its corresponding eigenvalue and wherein a n×n symmetric matrix gives n eigenvectors with corresponding n eigenvalues, n being any arbitrary integer. The three spherical coordinates comprises an angle a vector makes with the z-axis represented by $\rho$, an angle a vector makes with the x-axis represented by $\theta$, and the length of the vector represented by h.

The present invention will now be described more fully hereinafter with reference to the accompanying drawings in which a preferred embodiment of the invention is shown. This invention may, however, be embodied in many different forms and should not be construed as being limited to the embodiment set forth herein. Rather, the embodiment is provided so that this disclosure will be thorough, and will fully convey the scope of the invention to those skilled in the art.

The present invention provides an EEG based method to study and monitor functional aspects of the human brain in real time. Current technology is severely limited in being able to provide a decisive measure for every individual's neurological health by recording the functional behavior of the brain.

As shown in FIG. 1, EEG signals appear on the entire area of the scalp of every person, from where they are recorded using multiple sensors. The proposed invention looks for a mathematical structure within the various signals recorded from different locations on the scalp and classifies individuals as healthy and unhealthy. This system gives a quantitative assessment of a person's neurological health, which is something no EEG based system is known to provide. The concept is explained in the following steps:
 1. A set of sensors are placed on the scalp of a subject and signals emerging from the brain are recorded via an EEG device.
 2. The system begins to analyse the EEG signals and starts giving values for three parameters each for left and right side of the brain, namely, $\rho$, $\theta$, and h, which represent the underlying mathematical structure of the signals appearing on the scalp.
 3. The three parameters are plotted with time to give the novel 4 dimensional visualization of the entire EEG activity of the brain.
 4. The distribution of these three parameters is used to determine the systemic as well as mental health of a subject.

The following minimum components are required for the foregoing steps to be completed.
1. EEG Scanner—Electroencephalography scanner is used to monitor and record brain activity. EEG measures the brain activity of various neurons and then reports them back to the system for further interpretation.
2. Algorithm based processing unit—This is a system that analyses the mathematical structure of the signals being received from a subject's scalp and, in real-time, produces parameters that allow a medical practitioner to classify a subject as either healthy or unhealthy. It also gives a quantitative assessment of the degree of health or disorder of the individual. The 3 parameters can be computed for any localized area on the scalp or the entire scalp itself.

Example 1

Sampling of EEG Data of Subjects

Figure 2:
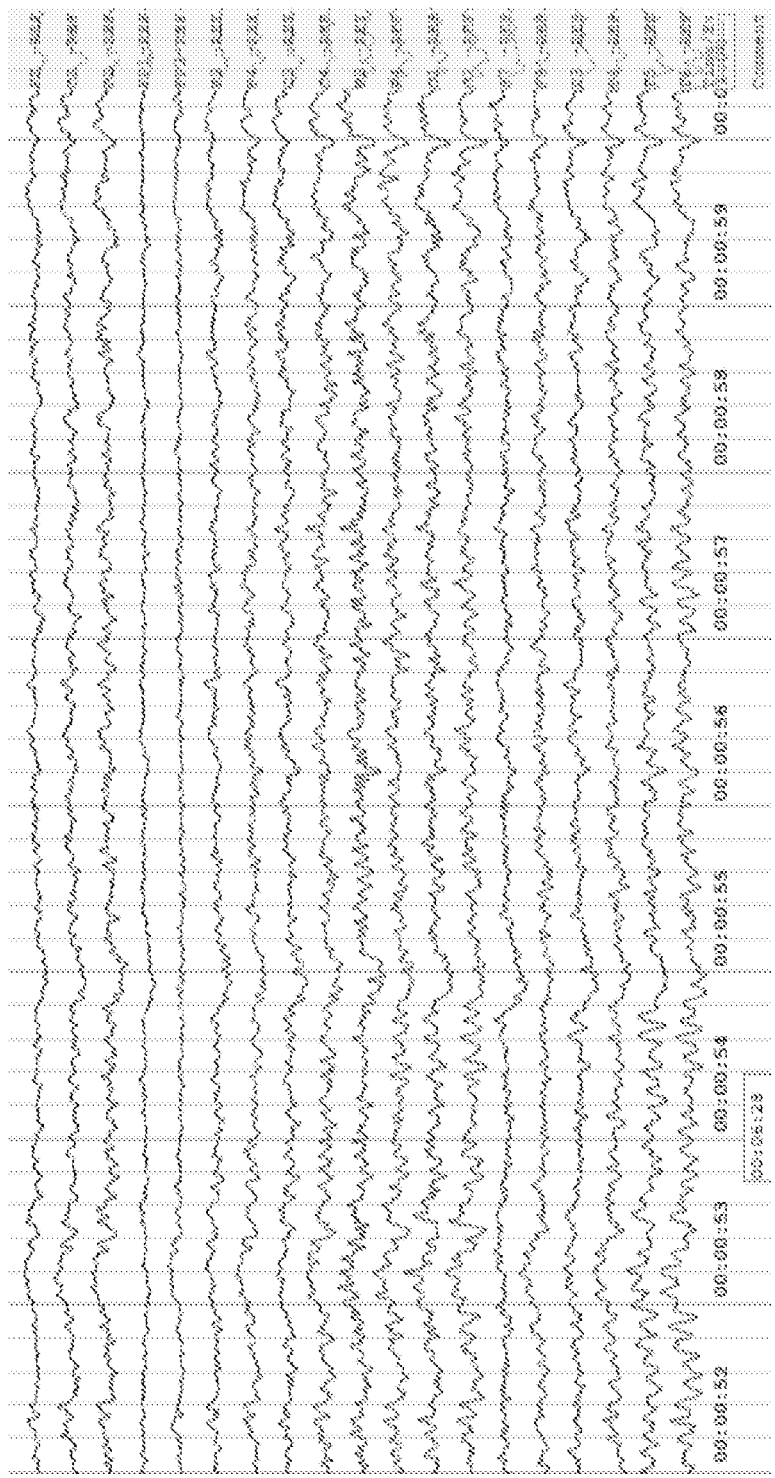
FIG. 2 depicts a sample of EEG signals recorded from a healthy subject.

The internationally recognized 10-20 system is used to place the sensors on the scalp and record the EEG signals. FIG. 2 shows a sample of the EEG signals recorded from a healthy subject. The name of each signal recorded is mentioned along with it on the extreme right of FIG. 2. First three signals, namely, Fz, Cz, Pz, lie along the line running at the centre of the scalp from the front to the back of the head. The signals ending with an odd number, for example, C3, lie on the left side of the scalp and those ending with an even number, for example, P4, lie on right side of the scalp.

Figure 3:
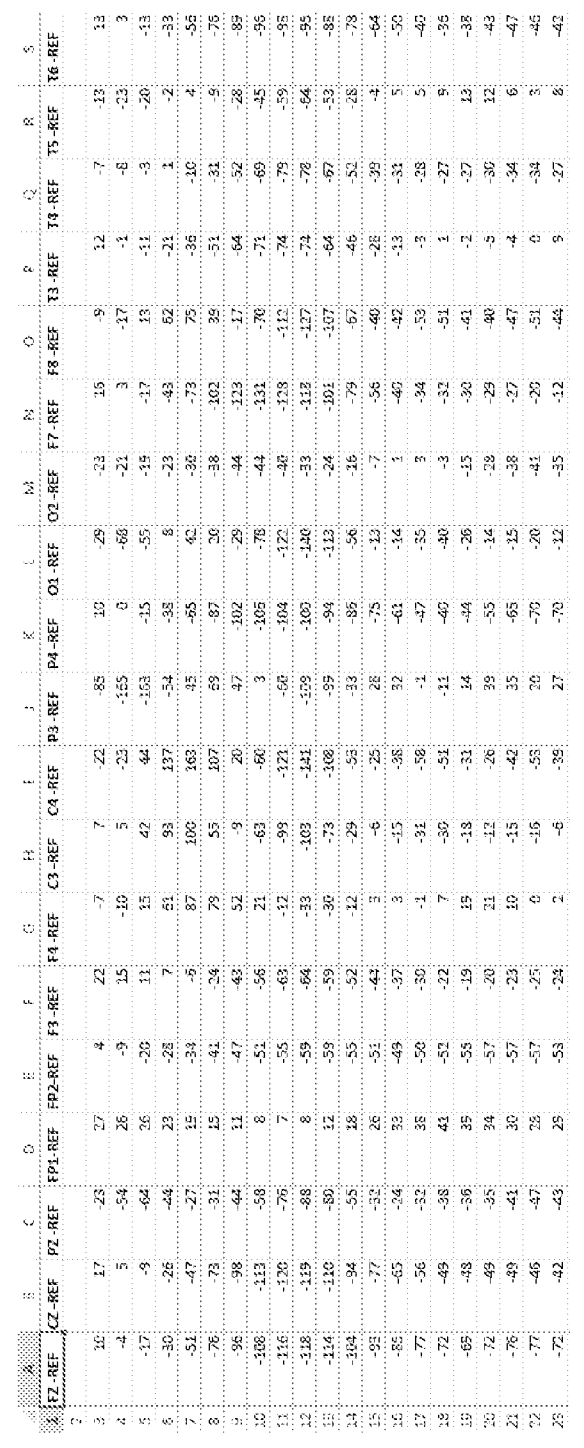

In this example, once the signals are recorded, they are separated into two groups, namely, left and right. The left group has all the signals that are obtained from the left side of the scalp, along with the signal Cz, and the right group has all the signals obtained from the right side of the scalp along with signal Cz. Therefore, each side has 9 signals each, listed as follows:
Left: Fp1, F7, F3, T3, C3, T5, P3, O1, Cz
Right: Fp2, F4, F8, C4, T4, P4, T6, O2, Cz It does not matter in which order the signals are placed within the group. Once the left group and right groups have been created, the algorithm works independently of the order in which signals are put in each group. In general, groups can be formed with any number of signals in them. Data is recorded on an EEG machine that records 256 samples of each signal per second. FIG. 3 shows the raw data of the signals represented in FIG. 2 that are used as input for the algorithm. This entire data is then broken into 'frames' that are the size of 1 second each for both the left and the right group. In other words, 1 second worth of data, i.e. 256 samples, of all the 9 signals in each group is taken separately and called a frame. The process that follows now describes just one frame taken from one of the groups, but applies identically to all the frames of both groups.

Example 2

Constructing Covariance Matrix of Sample EEG Data of Subjects

Figures 4, 5, 6:
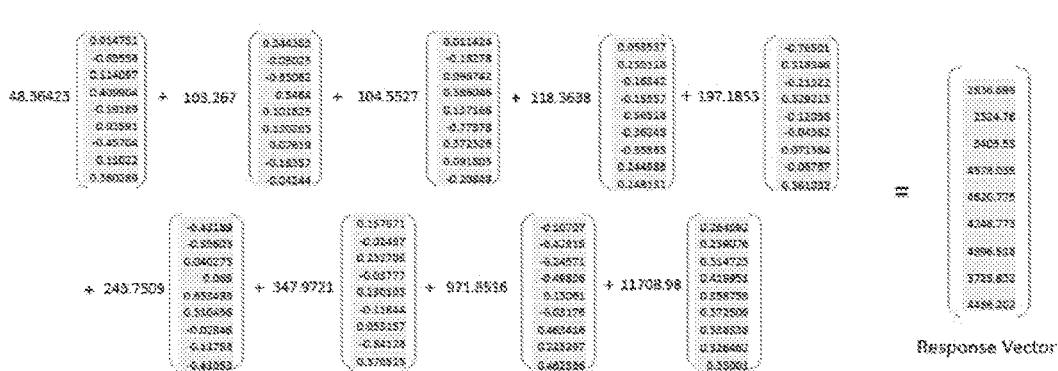
FIG. 4 shows 9×9 covariance matrix of the data obtained in FIG. 3.
FIG. 5 shows the 9 eigenvectors, with corresponding eigenvalues of the matrix in FIG. 4.
FIG. 6 shows the computation of the response vector of the covariance matrix in FIG. 4 from its eigenvectors and eigenvalues.

A covariance matrix is constructed with the 9 signals and 256 samples for each signal. FIG. 4 shows this covariance matrix. It is a symmetric 9×9 matrix that is populated with the covariance values of each signal with every other signal, computed using the 256 samples we have for all 9 signals. One can obtain the covariance between any two EEG signals by going to the row and column, with their respective names written next to each row and column of the matrix, and reading off that value from the matrix. For example, the covariance between F4 and C4 is 1301.435, and its location is at the $5^{th}$ column-$3^{rd}$ row and also, since the matrix is symmetric, $3^{rd}$ column-$5^{th}$ row.

With covariance matrix constructed we then proceed to compute its eigenvectors and eigenvalues. An eigenvector of a matrix is a vector which when multiplied by that matrix results in a scaled version of the original vector itself, i.e., $Ax_i = \lambda_i x_i$, where $x_i$ is one of the eigenvectors of A and $\lambda_i$ is its corresponding eigenvalue. A 9×9 symmetric matrix gives 9 eigenvectors with corresponding 9 eigenvalues. FIG. 5 show the 9 eigenvectors, with corresponding eigenvalues written on top, of the matrix in FIG. 4.

Example 3

Identifying Response Vector

Figure 7:
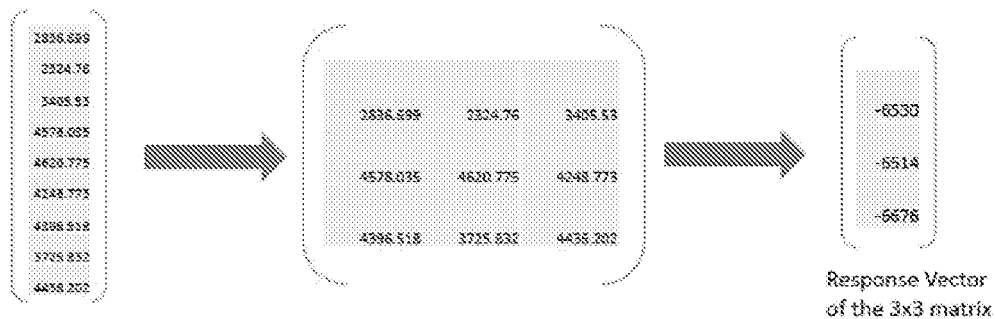
FIG. 7 depicts populated 3×3 matrix of rearrangement of values obtained in FIG. 6.
Figure 8:
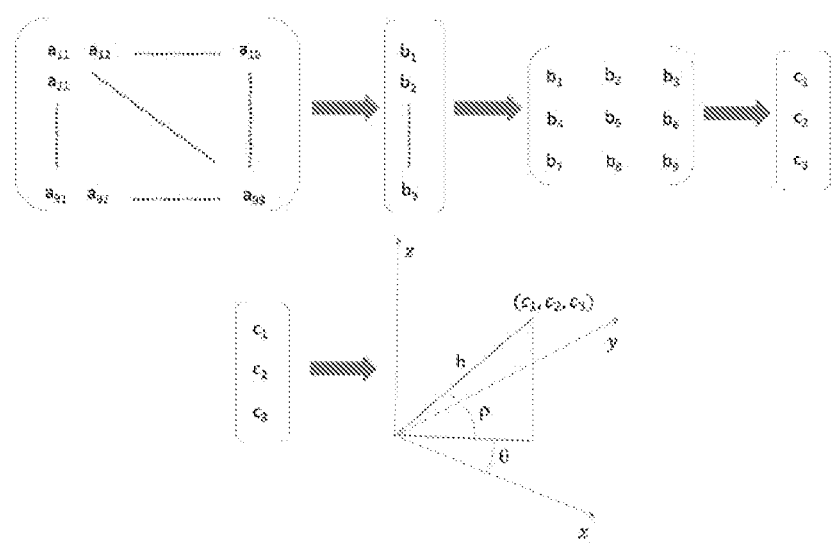
FIG. 8 shows process of taking a covariance matrix and reducing it to 3-dimensional spherical coordinates depicted in FIG. 7.

With all 9 eigenvectors and eigenvalues obtained, we first multiply each eigenvalue with its eigenvector and then add all the eigenvectors together, i.e., $\Sigma_i(\lambda_i v_i)$, to give what we call the responsevector$\Lambda$ of the covariance matrix. The eigenvectors corresponding to higher eigenvalues represent the slow changing aspect of the brain like unique brain signature of individual person, different chronic diseases and the eigenvectors with small eigenvalues represent the fast changing aspects of the brain like thought process, different diseases including mental diseases. If one needs to focus on one specific activity of the brain then individual eigenvectors are used instead of the response vectors, which represent the overall activity. FIG. 6 shows the computation of the response vector of the covariance matrix in FIG. 4 from its eigenvectors and eigenvalues. The response vector is of the same size as the eigenvectors, i.e., 9×1 and its elements can be rearranged to populate a 3×3 matrix, as shown in FIG. 7. Using the process outlined above, we now compute the 3×1 response vector of this 3×3 matrix. Then a transformation from Cartesian coordinate system to Spherical coordinate system is performed for this 3×1 response vector. The 3×1 response vector shown in FIG. 7 is (−6530, 6514, −6676) in Cartesian coordinates. When transformed to spherical coordinates the vector becomes (−35.9, −135.1, 11385). The first two coordinates, ρ and θ, are the angles this vector makes with the z and the x-axis respectively and the last coordinate is the length of the vector and is represented by h. This entire process of taking a covariance matrix and reducing it to 3-dimensional spherical coordinates is schematically depicted in FIG. 8.

Example 4

4D Visualization of EEG

Figure 9:
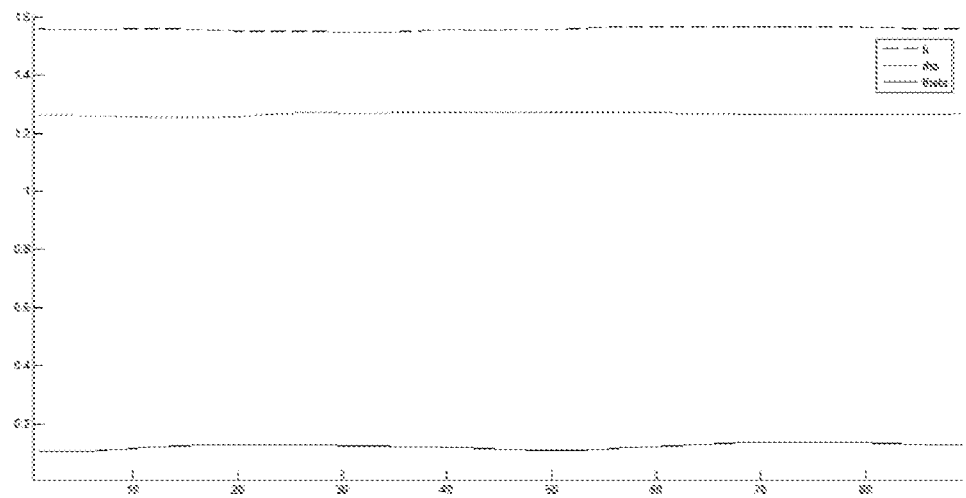
FIG. 9 shows the 4 D visualization for the left group of a subject.
Figure 10:
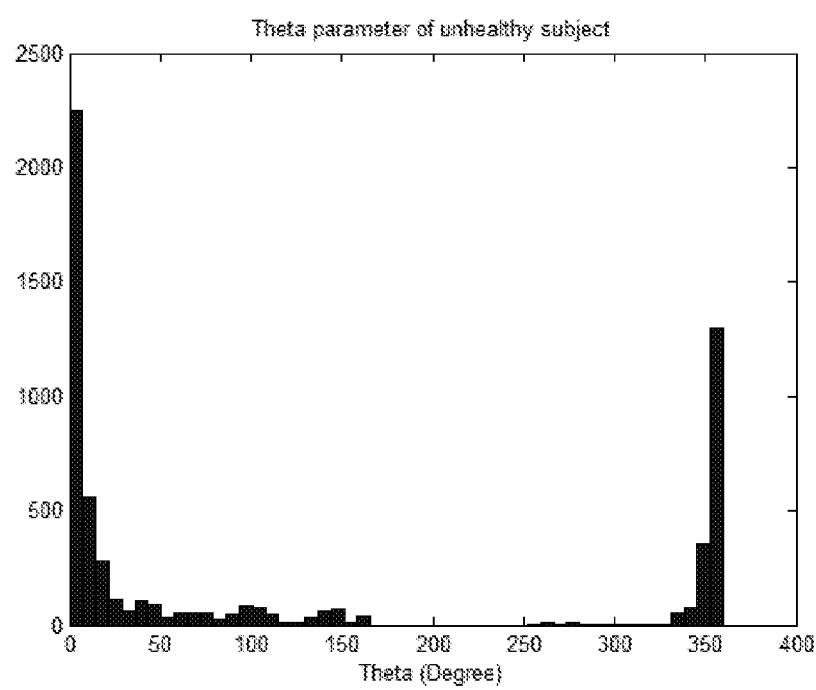
FIG. 10 shows the distribution of the θ parameter of an unhealthy subject who is suffering from epilepsy.
Figure 11:
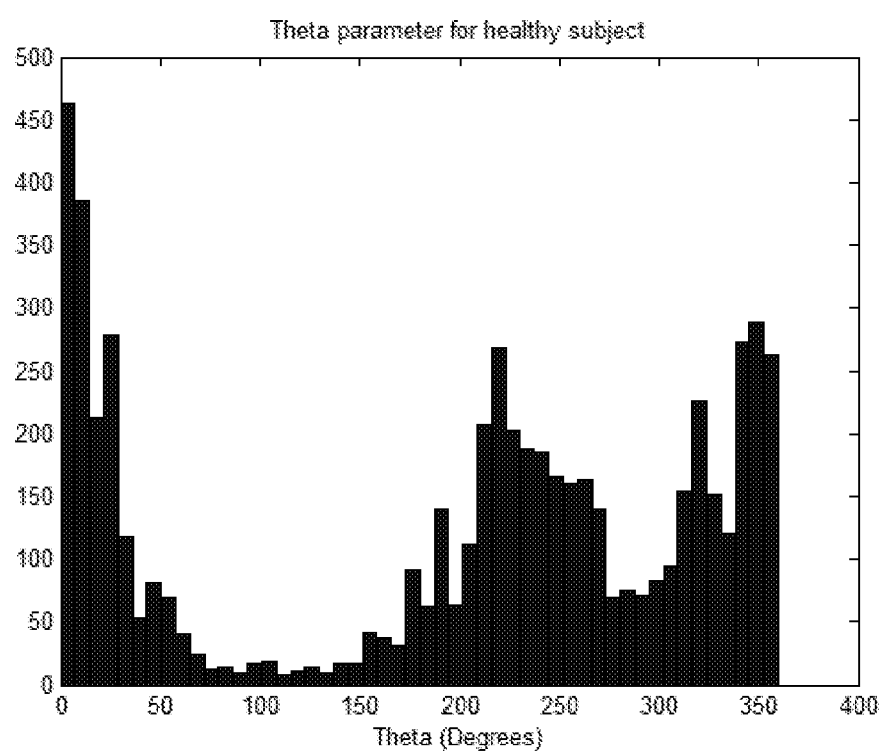
FIG. 11 shows the distribution of the same parameter of a healthy subject with no mental disorder.

The above process is carried out for all the frames of 1 second duration, and three parameters for each frame are computed. These three parameters for each frame are plotted as a function of time to give the 4 dimensional visualization of the EEG. FIG. 9 shows the 4 D visualization for the left group of a subject. The distribution of these parameters is used to diagnose unhealthy brains. FIG. 10 shows the distribution of the θ parameter of an unhealthy subject who is suffering from epilepsy and FIG. 11 shows the distribution of the same parameter of a healthy subject with no mental disorder. While looking at this figure it must be remembered that the θ parameter has a range from 0-360° and the distribution wraps around the end points of the range. One can clearly see that the distribution of the parameter of the unhealthy subject is Gaussian/Normal with mean around 0°, while the distribution for the healthy subject is much more widely distributed. These parameters were assessed in many healthy and unhealthy brains having diseases like epilepsy with but giving normal EEG, early Parkinson's disease and early dementia. These parameters were clearly different in different subjects suggesting the 4D EEG is helpful in diagnosing different diseases even in their early stages when EEG is showing normal findings.

The values of $\rho$ and $\theta$ for EEG data taken for one hour were also plotted that showed elongated bell shaped curve (Normal distribution). It was different for various diseases and healthy brains suggesting correlation between chemical components of brain and different diseases like low dopamine in Parkinson's disease and low acetylcholine in Alzheimer and dementia.

We claim:

1. An EEG based diagnosis system for early detection of human disorders comprising:
   a. a means for sensing brainwaves of a user, the brainwaves comprising EEG signals;
   b. a means for recording a pattern of the brainwaves of the user;
   c. a means for processing the pattern recorded in step b., the means for processing capable of performing an analysis of the pattern of the brainwaves resulting in a four dimensional visualization of the entire EEG activity of the user's brain; and
   d. a means for representing the four dimensional visualization of the entire EEG activity of the user's brain obtained in step c.;
   characterized in that the analysis of the pattern is done by creating a covariance matrix, computing eigen values and reducing the covariance matrix to three dimensional spherical coordinate eigen value parameters, giving values for three parameters each for the left and right side of the brain, namely, p, $\theta$, and h, and plotting them with time to give the four dimensional visualization of brain activity, wherein any deviation in distribution pattern of said eigen parameters is an indicator of a disorder, and
   wherein said analysis further includes statistical, temporal and spectral property assessment of the pattern through four dimensional visualisation of eigen vectors/eigen values, and properties of inner product spaces plotted with time.

2. The EEG based system as claimed in claim 1, wherein said means for sensing and said means for recording a pattern of the brainwaves comprise an Electroencephalograph (EEG).

3. The EEG based system as claimed in claim 1, wherein the means for sensing and the means for recording a pattern of the brainwaves include spinal EEG and different scalp EEG electrodes.

4. The EEG based system as claimed in claim 1, wherein said means for processing the pattern comprises a programmed processing unit.

5. The EEG based system as claimed in claim 1, wherein multiple output data resulting from recorded EEG patterns are taken together and a structure of their covariance and higher-order statistics matrices are analysed through eigen values, eigenvector, eigen direction and eigen spaces and other signal processing techniques including, but not limited to, fast Fourier transform, compression sensing, and wavelet transform, to obtain said four dimensional visualization.

6. The EEG based system as claimed in claim 1, wherein the analysis further includes a step of creating a correlation matrix from EEG signals obtained in a fixed duration of time from various locations of the user's brain.

7. The EEG based system as claimed in claim 1, wherein the means for representing the four dimensional visualization of the entire EEG activity of the user's brain is an output device selected from the group comprising a printer, a visual output screen, an audio-visual output device or a combination thereof.

8. An EEG based diagnostic kit for early detection of human disorders comprising:
   a. a means for sensing brainwaves of a user, the brainwaves comprising EEG signals;
   b. a means for recording a pattern of the brainwaves of the user;
   c. a means for processing the pattern recorded in step b., the means for processing capable of performing an analysis of the pattern resulting in a four dimensional visualization of the entire EEG activity of the user's brain; and
   d. a means for representing the four dimensional visualization of the entire EEG activity of the user's brain obtained in step c.;
   wherein:
   the means for sensing and the means for recording a pattern of the brainwaves include spinal EEG and different scalp EEG electrodes;
   said means for processing the pattern comprises a programmed processing unit;
   said analysis includes generating three parameters each for the left and right side of the brain, namely p, $\theta$, and h, and plotting them with time to give the four dimensional visualization of brain activity, and further includes statistical, temporal and spectral property assessment of the pattern through four dimensional visualization of eigen vectors/eigen values, and properties of inner product spaces plotted with time; and
   the means for representing the four dimensional visualization of the entire EEG activity of the user's brain is an output device selected from the group comprising a printer, a visual output screen, an audio-visual output device or a combination thereof.

* * * * *